US012678394B2

(12) United States Patent
Halder Joshi et al.

(10) Patent No.: US 12,678,394 B2
(45) Date of Patent: Jul. 14, 2026

(54) COSMETIC COMPOSITION COMPRISING AT LEAST ONE SILICONE OF SPECIFIC FORMULA, AT LEAST ONE AMINOSILICONE, AT LEAST ONE PARTICULAR COPOLYMER, AND AT LEAST ONE POLYOL

(71) Applicant: L'OREAL, Paris (FR)

(72) Inventors: Shilpa Halder Joshi, Mumbai (IN); Anand Mahadeshwar, Clark, NJ (US); Gaelle Brisse, Mumbai (IN); Ritesh Tolani, Mumbai (IN); Kishor Dagwar, Mumbai (IN)

(73) Assignee: L'OREAL, Paris (FR)

( * ) Notice: Subject to any disclaimer, the term of this patent is extended or adjusted under 35 U.S.C. 154(b) by 295 days.

(21) Appl. No.: 18/522,346

(22) Filed: Nov. 29, 2023

(65) Prior Publication Data

US 2024/0325284 A1 Oct. 3, 2024

(30) Foreign Application Priority Data

Mar. 27, 2023 (IN) ............................. 202311021890
May 26, 2023 (FR) ....................................... 2305254

(51) Int. Cl.

| | |
|---|---|
| ***A61K 8/898*** | (2006.01) |
| ***A61K 8/34*** | (2006.01) |
| ***A61K 8/81*** | (2006.01) |
| ***A61K 8/892*** | (2006.01) |
| ***A61Q 5/00*** | (2006.01) |

(52) U.S. Cl.

CPC .............. *A61K 8/898* (2013.01); *A61K 8/345* (2013.01); *A61K 8/8141* (2013.01); *A61K 8/892* (2013.01); *A61Q 5/00* (2013.01); *A61K 2800/594* (2013.01)

(58) Field of Classification Search

CPC ...... A61K 8/898; A61K 8/345; A61K 8/8141; A61K 8/892; A61K 2800/594; A61K 8/8158; A61Q 5/00

See application file for complete search history.

(56) References Cited

U.S. PATENT DOCUMENTS

| | | | | |
|---|---|---|---|---|
| 10,561,597 B2 * | 2/2020 | Blondel et al. | .......... | A61K 8/06 424/401 |
| 2019/0194457 A1 * | 6/2019 | Huggins et al. | ........ | C08L 83/04 424/401 |

* cited by examiner

*Primary Examiner* — James H Alstrum-Acevedo
(74) *Attorney, Agent, or Firm* — POLSINELLI PC

(57) ABSTRACT

The present invention relates to a cosmetic composition comprising:
(a) at least one silicone of formula (X);
(b) at least one aminosilicone;
(c) at least one copolymer comprising at least one monomer of 2-acrylamido-2-methylpropanesulfonic acid, at least one monomer with a hydrophobic group and at least one ethylenically unsaturated monomer which does not comprise any hydrophobic groups; and
(d) at least one polyol.

20 Claims, No Drawings

COSMETIC COMPOSITION COMPRISING AT LEAST ONE SILICONE OF SPECIFIC FORMULA, AT LEAST ONE AMINOSILICONE, AT LEAST ONE PARTICULAR COPOLYMER, AND AT LEAST ONE POLYOL

This application claims priority to application No. 202311021890 filed in India on Mar. 27, 2023, under 35 U.S.C. § 119, and Application No. 2305254 filed in France on May 26, 2023, under 35 U.S.C. § 119. The entire contents of which are hereby incorporated by reference.

The present invention relates to a cosmetic composition comprising at least one silicone of specific formula, at least one aminosilicone, at least one particular copolymer, and at least one polyol.

The invention also relates to the cosmetic process for treating keratin fibres comprising the step of applying said cosmetic composition to the keratin fibres and to the use of said cosmetic composition for the cosmetic treatment of keratin fibres and to a device suitable for applying said cosmetic composition to keratin fibres.

TECHNICAL FIELD

Keratin fibres, notably human keratin fibres such as the hair, are subject to many external aggressors throughout day-to-day activities which can lead to difficulties in combing and keeping the hair manageable, smooth, and soft.

In the field of the cosmetic treatment of keratin fibres, and more particularly in the field of hair washing and/or haircare, rinse-out products but also leave-in products are used. These products aim to provide various cosmetic properties, notably smoothness, sheen, softness, suppleness, lightness, a natural feel and good disentangling properties.

However, with increasing regulations concerning the use of raw materials, in particular silicones, cosmetics companies are looking for alternative cosmetic formulations to replace conventional cyclopentasiloxane-based serums. Cosmetics companies are seeking to offer compliant, suitable formulations while retaining cosmetic sensory benefits.

Nevertheless, most formulations lead to compositions with insufficient cosmetic sensory benefits, notably in terms of anti-frizz properties and conditioning of the hair. Indeed, the hair remains dull and difficult to style.

There is thus a need to develop cosmetic compositions, particularly leave-in compositions, that achieve superior anti-frizz, curl-opening and conditioning properties and lead to easy-to-style, smooth, soft, shiny hair.

The Applicant has now discovered that a composition containing at least one silicone of specific formula, at least one aminosilicone, at least one particular copolymer, and at least one polyol, makes it possible to obtain products which impart excellent cosmetic sensory benefits to the hair. In particular, the hair treated with the compositions according to the invention is smooth, soft, shiny, very manageable and easy-to-style and possesses good anti-frizz properties.

DISCLOSURE OF THE INVENTION

The present invention relates to a cosmetic composition comprising:

(a) at least one silicone of formula (X) as defined hereinafter;

(b) at least one aminosilicone;

(c) at least one copolymer comprising at least one monomer of 2-acrylamido-2-methylpropanesulfonic acid, at least one monomer with a hydrophobic group and at least one ethylenically unsaturated monomer which does not comprise any hydrophobic groups; and (d) at least one polyol.

The composition of the invention makes it possible to impart to hair good cosmetic properties, such as smoothness, sheen, softness, suppleness, lightness, a natural feel and good disentangling and manageability properties. Moreover, the composition is clear and transparent and has an agreeable texture which make it easier to apply.

A subject of the present invention relates to a cosmetic process for treating keratin fibres comprising the step of applying said cosmetic composition to the keratin fibres.

A subject of the present invention is also the use of said cosmetic composition to treat keratin fibres, in particular human keratin fibres such as the hair.

Another subject of the present invention relates to a dropper device suitable for applying said cosmetic composition to the keratin fibres such as the hair and delivering said composition in a dropwise manner.

Other subjects, characteristics, aspects, and advantages of the invention will emerge even more clearly on reading the description and the examples that follow.

In the text hereinbelow, unless otherwise indicated, the limits of a range of values are included in that range, notably in the expressions "between" and "ranging from . . . to . . . ".

Moreover, the expression "at least one" used in the present description is equivalent to the expression "one or more".

"Cosmetically acceptable" means that the item in question is compatible with any keratin material. For example, "cosmetically acceptable medium" means a medium that is compatible with any keratinous substrate, and, in particular, human hair.

"Conditioning" as used herein means imparting to at least one keratinous fiber at least one property chosen from combability, manageability, moisture-retentivity, luster, shine, smoothness and softness. The state of conditioning could be evaluated by measuring, and comparing, for example the surface state of the treated hair and of the untreated hair in terms of average maximum force (newton) using a sliding bench.

"Silicone compound," as used herein, includes, for example, silanes, siloxanes, and organosiloxanes.

Silicone (a)

According to the present invention, the composition comprises at least one silicone (a) of formula (X) below:

(X)

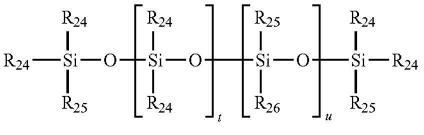

in which:

$R_{24}$, which is identical or different, denotes a $C_1$-$C_{10}$ alkyl radical, preferably a $C_1$-$C_4$ alkyl radical, even more preferably a methyl radical;

$R_{26}$, which is identical or different, denotes an aryl group, it being possible for this aryl group to comprise one or more optionally substituted aryl rings;

$R_{25}$, which is identical or different, denotes $R_{26}$, $R_{24}$ or —$OSi(R_{24})_3$;

t varies from 0 to 1000; preferably t equals 0;

u varies from 1 to 1000; preferably, u varies from 1 to 10;

and the sum of t+u can vary from 1 to 2000; preferably from 1 to 10.

The substituents of the aryl groups can be alkyl, alkenyl, acyl, ketone, halogen (for example, Cl and Br), or amine groups. Examples of aryl groups are phenyl, a phenyl group substituted by $C_1$-$C_5$ alkyl radicals or $C_1$-$C_5$ alkenyl radicals such as allylphenyl, methylphenyl, ethylphenyl, or vinylphenyl, and their mixtures.

$R_{26}$ preferably denotes an aryl group not substituted.

$R_{24}$ preferably denotes a methyl radical.

$R_{26}$ preferably denotes a phenyl, naphtyl, benzyl or phenethyl radical, more preferably a phenyl radical.

$R_{25}$ preferably denotes a methyl, phenyl, or a —OSi$(CH_3)_3$ radical.

Preferably, all $R_{24}$ denote a methyl radical, and $R_{26}$ denotes a phenyl, naphtyl, benzyl or phenethyl radical, more preferably a phenyl radical; and $R_{25}$ denotes a methyl, a phenyl or a —OSi$(CH_3)_3$ radical; and preferably t equals 0 and u varies from 1 to 10.

More particularly, the sum t+u varies from 1 to 1000.

Use may be made, amongst the silicones of formula (X) as defined above, of, for example (INCI names):

phenyl trimethicone:

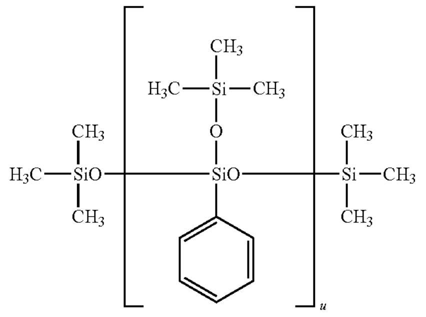

where u varies from 1 to 10, preferably, u equals 1, or diphenyl dimethicone:

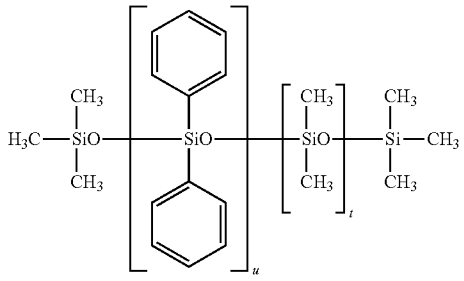

where u varies from 1 to 10 and t varies from 1 to 10, preferably, u and t equal 1, or phenyl methicone:

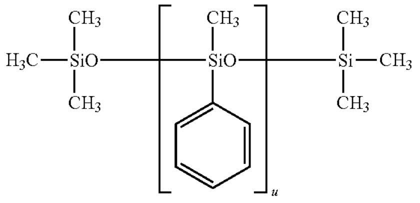

where u varies from 1 to 10, preferably, u equals 1.

Mention may be made, as example of these compounds, of those sold by the company Bayer under the name Baysilone Fluid PD5 Oil, by the company Dow Corning under the name Dow Corning 556 Fluid, by Rhône-Poulenc under the names Mirasil DPDM, Rhodorsil Oil 510 V 100, Rhodorsil Oil 550, Rhodorsil Oil 510V500, or Rhodorsil Oil 710, or by the company Wacker under the names Wacker Belsil PDM 20, PDM 200, or PDM 1000.

In a preferred embodiment, the at least one silicone (a) according to the invention is phenyl trimethicone.

Advantageously, the total amount of silicone(s) (a) in the composition ranges from 1 to 40% by weight, preferably from 1 to 30% by weight, more preferably from 2 to 20% by weight, even more preferably from 2.5 to 15% by weight, better from 3 to 10% by weight, even better from 4 to 6% by weight, relative to the total weight of the composition.

Advantageously, the total amount of phenyl trimethicone in the composition ranges from 1 to 40% by weight, preferably from 1 to 30% by weight, more preferably from 2 to 20% by weight, even more preferably from 2.5 to 15% by weight, better from 3 to 10% by weight, even better from 4 to 6% by weight, relative to the total weight of the composition.

Aminosilicone (b)

According to the present invention, the composition comprises at least one aminosilicone (b). The term "aminosilicone" denotes any silicone including at least one primary, secondary or tertiary amine or a quaternary ammonium group.

The weight-average molecular masses of these aminosilicones may be measured by gel permeation chromatography (GPC) at room temperature (25° C.), as polystyrene equivalent. The columns used are μ styragel columns. The eluent is THF and the flow rate is 1 ml/min. 200 μl of a 0.5% by weight solution of silicone in THF are injected. Detection is performed by refractometry and UV-metry.

Preferably, the aminosilicone(s) (b) that may be used in the context of the invention are chosen from:

a) the polysiloxanes corresponding to formula (A):

(A)

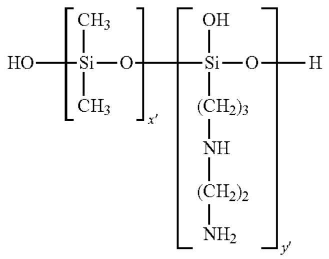

in which x' and y' are integers such that the weight-average molecular weight (Mw) is between 5000 and 500 000 approximately;

b) the aminosilicones corresponding to formula (B):

$$R'_aG_{3-a}\text{-}Si(OSiG_2)_n\text{—}(OSiG_bR'_{2-b})_m\text{—}O\text{—}SiG_{3-a'}\text{-}R'_{a'} \quad (B)$$

in which:

G, which may be identical or different, denotes a hydrogen atom or a phenyl, OH, $C_1$-$C_8$ alkyl, for example methyl, or $C_1$-$C_8$ alkoxy, for example methoxy, group;

a and a', which may be identical or different, denote 0 or an integer from 1 to 3, in particular 0, with the proviso that at least one from among a and a' is equal to zero, b denotes 0 or 1, in particular 1, m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

R', which may be identical or different, denotes a monovalent radical of formula —$C_qH_{2q}$L in which q is a number ranging from 2 to 8 and L is an optionally quaternized amine group chosen from the following groups:

—NR"-Q-N(R")$_2$,
—N(R")$_2$,
—$N^+$(R")$_3$ $A^-$,
—$N^+$H(R")$_2$ $A^-$,
—$N^+H_2$(R") $A^-$,
—NR"-Q-$N^+$(R")$H_2$ $A^-$,
—NR"-Q-$N^+$(R")$_2$H $A^-$ and
—NR"-Q-$N^+$(R")$_3$ $A^-$, in which R", which may be identical or different, denotes hydrogen, phenyl, benzyl, or a saturated monovalent hydrocarbon-based radical, for example a $C_1$-$C_{20}$ alkyl radical; Q denotes a linear or branched group of formula $C_rH_{2r}$, r being an integer ranging from 2 to 6, preferably from 2 to 4; and A− represents a cosmetically acceptable anion, notably a halide anion such as fluoride, chloride, bromide or iodide.

Preferably, the aminosilicone(s) (b) are chosen from the aminosilicones of formula (B). Preferably, the aminosilicones of formula (B) are chosen from the aminosilicones corresponding to formulae (C), (D), (E), (F) and/or (G) below.

According to a first embodiment, the aminosilicones corresponding to formula (B) are chosen from the silicones known as "trimethylsilyl amodimethicone" corresponding to formula (C):

(C)

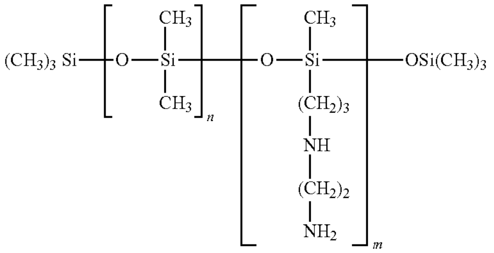

in which m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10.

According to a second embodiment, the aminosilicones corresponding to formula (B) are chosen from the silicones of formula (D) below:

(D)

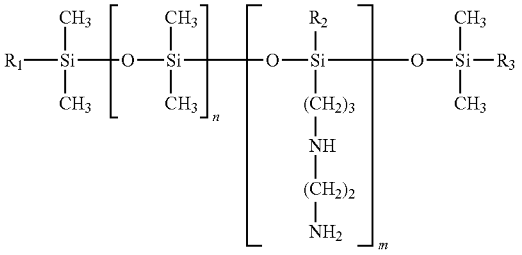

in which:

m and n are numbers such that the sum (n+m) ranges from 1 to 1000, in particular from 50 to 250 and more particularly from 100 to 200; n possibly denoting a number from 0 to 999, notably from 49 to 249 and more particularly from 125 to 175, and m possibly denoting a number from 1 to 1000, notably from 1 to 10 and more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical, preferably a methoxy radical.

The hydroxy/alkoxy mole ratio preferably ranges from 0.2:1 to 0.4:1 and preferably from 0.25:1 to 0.35:1 and more particularly is equal to 0.3:1.

The weight-average molecular mass (Mw) of these silicones preferably ranges from 2000 to 1 000 000 and more particularly from 3500 to 200 000.

According to a third embodiment, the aminosilicones corresponding to formula (B) are chosen from the silicones of formula (E) below:

(E)

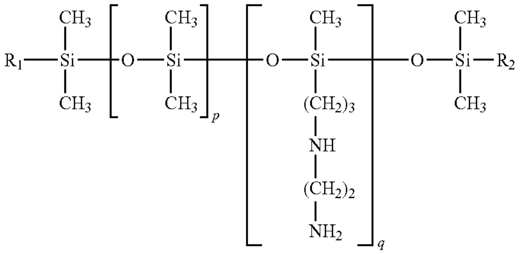

in which:

p and q are numbers such that the sum (p+q) ranges from 1 to 1000, in particular from 50 to 350 and more particularly from 150 to 250; p possibly denoting a number from 0 to 999 and notably from 49 to 349 and more particularly from 159 to 239, and q possibly denoting a number from 1 to 1000, notably from 1 to 10 and more particularly from 1 to 5;

$R_1$ and $R_2$, which are different, represent a hydroxyl or $C_1$-$C_4$ alkoxy radical, at least one of the radicals $R_1$ or $R_2$ denoting an alkoxy radical, preferably a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular weight (Mw) of the silicone preferably ranges from 2000 to 200 000, even more particularly from 5000 to 100 000 and more particularly from 10 000 to 50 000.

The commercial products comprising silicones of structure (D) or (E) may include in their composition one or more other aminosilicones the structure of which is different from formula (D) or (E).

A product containing aminosilicones of structure (D) is sold by the company Wacker under the name Belsil® ADM 652.

A product containing aminosilicones of structure (E) is sold by Wacker under the name Fluid WR 1300® or under the name Belsil® ADM LOG 1.

When these aminosilicones are used, one particularly advantageous embodiment consists in using them in the form of an oil-in-water emulsion. The oil-in-water emulsion may comprise one or more surfactants. The surfactants may be of any nature but are preferably cationic and/or non-ionic. The number-average size of the silicone particles in the emulsion generally ranges from 3 nm to 500 nm. Preferably, notably as aminosilicones of formula (E), use is made of microemulsions with a mean particle size ranging from 5 nm to 60 nm (limits included) and more particularly from 10 nm to 50 nm (limits included). Thus, use may be made according to the invention of the aminosilicone microemulsions of formula (E) sold under the names Finish CT 96 E® or SLM 28020® by the company Wacker.

According to a fourth embodiment, the aminosilicones corresponding to formula (B) are chosen from the silicones of formula (F) below:

(F)

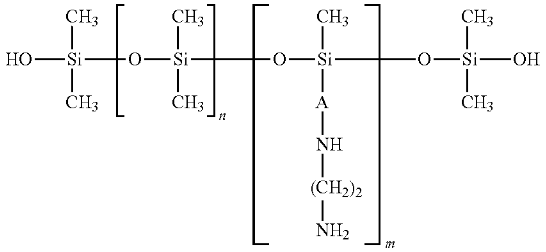

in which:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably linear.

The weight-average molecular mass (Mw) of these aminosilicones preferably ranges from 2000 to 1 000 000 and even more particularly from 3500 to 200 000.

Another silicone corresponding to formula (B) is, for example, the Xiameter MEM 8299 Emulsion from Dow Corning (INCI name: amodimethicone and trideceth-6 and cetrimonium chloride).

According to a fifth embodiment, the aminosilicones corresponding to formula (B) are chosen from the silicones of formula (G) below:

(G)

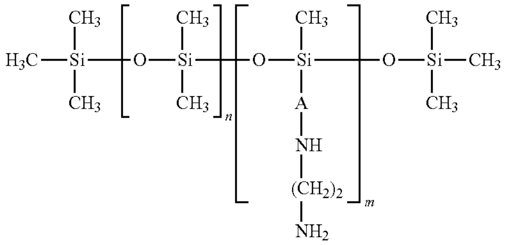

in which:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical, preferably branched, containing from 4 to 8 carbon atoms and preferably 4 carbon atoms.

The weight-average molecular mass (Mw) of these aminosilicones preferably ranges from 500 to 1 000 000 and even more particularly from 1000 to 200 000.

A silicone corresponding to this formula is, for example, DC2-8566 Amino Fluid from Dow Corning;

c) the aminosilicones corresponding to formula (H):

(H)

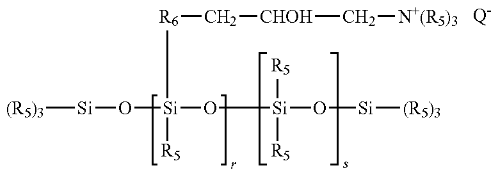

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$Q^-$ is an anion, such as a halide ion, in particular a chloride ion, or an organic acid salt, in particular an acetate;

r represents a mean statistical value ranging from 2 to 20 and in particular from 2 to 8;

s represents a mean statistical value ranging from 20 to 200 and in particular from 20 to 50.

Such aminosilicones are notably described in patent U.S. Pat. No. 4,185,087.

d) the quaternary ammonium silicones of formula (I):

(I)

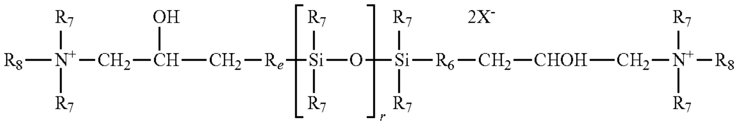

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represent a hydrogen atom, a monovalent hydrocarbon-based radical having from 1 to 18 carbon atoms, and in particular a $C_1$-$C_{18}$ alkyl radical, a $C_2$-$C_{18}$ alkenyl radical or a radical —$R_6$—$NHCOR_7$;

$X^-$ is an anion such as a halide ion, notably chloride, or an organic acid salt, notably acetate;

r represents a mean statistical value ranging from 2 to 200 and in particular from 5 to 100.

These silicones are described, for example, in patent application EP-A 0 530 974;

e) the aminosilicones of formula (J):

(J)

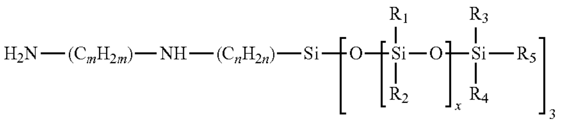

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and x is chosen such that the amine number ranges from 0.01 to 1 meq/g;

f) multiblock polyoxyalkylene aminosilicones, of the type $(AB)_n$, A being a polysiloxane block and B being a polyoxyalkylene block including at least one amine group.

Said silicones are preferably formed from repeating units having the following general formulae:

$$[—(SiMe_2O)_xSiMe_2—R—N(R'')—R'—O(C_2H_4O)_a(C_3H_6O)_b—R'—N(H)—R—]$$

or alternatively $$[—(SiMe_2O)_xSiMe_2—R'—N(R'')—R'—O(C_2H_4O)_a(C_3H_6O)_b—]$$

in which:

a is an integer greater than or equal to 1, preferably ranging from 5 to 200 and more particularly ranging from 10 to 100;

b is an integer between 0 and 200, preferably ranging from 4 to 100 and more particularly between 5 and 30;

x is an integer ranging from 1 to 10 000 and more particularly from 10 to 5000;

R'' is a hydrogen atom or a methyl;

R, which may be identical or different, represent a linear or branched divalent $C_2$-$C_{12}$ hydrocarbon-based radical, optionally including one or more heteroatoms such as oxygen; preferably, R denotes an ethylene radical, a linear or branched propylene radical, a linear or branched butylene radical or a $CH_2CH_2CH_2OCH_2CH(OH)CH_2$— radical; preferentially, R denotes a $CH_2CH_2CH_2OCH_2CH(OH)CH_2$— radical;

R', which may be identical or different, represent a linear or branched divalent $C_2$-$C_{12}$ hydrocarbon-based radical, optionally including one or more heteroatoms such as oxygen; preferably, R' denotes an ethylene radical, a linear or branched propylene radical, a linear or branched butylene radical or a radical $CH_2CH_2CH_2OCH_2CH(OH)CH_2$—; preferentially, R' denotes —$CH(CH_3)$—$CH_2$—.

The siloxane blocks preferably represent between 50 mol % and 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular mass (Mw) of the silicone is preferably between 5000 and 1 000 000 and more particularly between 10 000 and 200 000.

Mention may notably be made of the silicones sold under the name Silsoft A-843 or Silsoft A+ by Momentive.

g) and mixtures thereof.

Preferably, the aminosilicones of formula (B) are chosen from the aminosilicones corresponding to formula (E).

Preferably, the composition according to the invention comprises at least one aminosilicone (b) having the INCI name amodimethicone, preferably introduced in the form of an emulsion or microemulsion with surfactants.

Preferably, the composition according to the invention comprises at least one aminosilicone (b) having the INCI name amodimethicone as an emulsion or microemulsion with surfactants, having the INCI names trideceth-5 and trideceth-10.

Preferably, the composition comprises aminosilicone(s) (b) selected from amodimethicones, preferably selected from the aminosilicones of formulae (C), (D), (E), (G) and mixtures thereof, more preferably selected from the aminosilicones of formula (E) and mixtures thereof.

Advantageously, the total amount of aminosilicone(s) (b) in the composition ranges from 0.01 to 30% by weight, preferably from 0.05 to 20% by weight, more preferably from 0.1 to 10% by weight, even more preferably from 0.5 to 6% by weight, better from 1 to 4% by weight, relative to the total weight of the composition.

Advantageously, the total amount of amodimethicone(s) in the composition ranges from 0.01 to 30% by weight, preferably from 0.05 to 20% by weight, more preferably from 0.1 to 10% by weight, even more preferably from 0.5 to 6% by weight, better from 1 to 4% by weight, relative to the total weight of the composition.

Copolymer (c)

According to the present invention, the composition comprises at least one copolymer (c) comprising at least one monomer of 2-acrylamido-2-methylpropanesulfonic acid, at least one monomer with a hydrophobic group and at least one ethylenically unsaturated monomer which does not comprise any hydrophobic groups.

Within the context of the present invention, the term "hydrophobic group" is understood to be a hydrocarbon-based, branched or unbranched, saturated or unsaturated fatty chain comprising from 6 to 50 carbon atoms.

The copolymer(s) (c) may be crosslinked in the presence of a crosslinking agent.

The term "crosslinked copolymer" is understood to be a non-linear copolymer which is in the form of a three-dimensional network that is insoluble in water but swellable in water, leading to the production of a chemical gel.

The crosslinking agent is chosen from polyolefinically unsaturated compounds commonly used for the crosslinking of polymers obtained by radical polymerization.

The crosslinking agent is more particularly chosen from ethylene glycol dimethacrylate, tetraallyloxyethane, ethylene glycol diacrylate, diallylurea, triallylamine, trimethylolpropane triacrylate or methylenebisacrylamide, or a mixture of these compounds.

Preferably, the crosslinking agent is trimethylolpropane triacrylate.

Preferably, the copolymer(s) (c) are crosslinked by a crosslinking agent, preferably trimethylolpropane triacrylate.

The 2-acrylamido-2-methylpropanesulfonic acid monomer(s) of the copolymer (c) contained in the composition in accordance with the invention are in free form or are partially or completely neutralized by an inorganic base (sodium hydroxide, potassium hydroxide or aqueous ammonia) or an organic base, such as mono-, di- or triethanolamine, an aminomethylpropanediol, N-methylglucamine, basic amino acids, such as arginine and lysine, and the mixture of these compounds.

According to the invention, the 2-acrylamido-2-methylpropanesulfonic acid monomers preferably correspond to the following general formula (1):

(1)

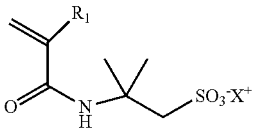

In which $X^+$ denotes a cationic counterion, in particular an alkali metal or alkaline-earth metal, or an ammonium, preferably ammonium, or a mixture of cations; $R_1$ denotes a hydrogen atom or a linear or branched $C_1$-$C_6$ alkyl radical such as methyl, and $R_1$ preferably denotes a hydrogen atom.

Preferably, the 2-acrylamido-2-methylpropanesulfonic acid monomer(s) according to the invention are partially or completely salified in the form of the ammonium salt.

Preferably, the 2-acrylamido-2-methylpropanesulfonic acid monomer(s) according to the invention are completely salified, preferably in the form of the ammonium salt.

AMPS® may be cited as an example of 2-acrylamido-2-methylpropanesulfonic acid monomer(s).

The copolymer(s) (c) comprise at least one monomer with a hydrophobic group which is preferably an ethylenically unsaturated monomer comprising at least one fatty hydrocarbon-based chain comprising from 6 to 50 carbon atoms, preferably from 6 to 22 and more particularly from 12 to 18 carbon atoms.

The monomer with a hydrophobic group is preferably chosen from the acrylates or acrylamides of formula (2):

(2)

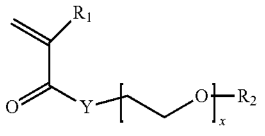

in which $R_1$ denotes a hydrogen atom or a linear or branched $C_1$-$C_6$ alkyl radical, preferably methyl; Y denotes O or NH; $R_2$ denotes a hydrocarbon-based radical comprising from 6 to 50 carbon atoms and more preferably from 6 to 22 carbon atoms and even more preferably from 12 to 18 carbon atoms; x denotes a number ranging from 0 to 100.

According to one particular embodiment of the invention, in formula (2), Y denotes an oxygen atom.

According to one particular embodiment of the invention, in formula (2), the $R_1$ group represents a methyl.

According to one particular embodiment of the invention, x represents an integer between 3 and 25, and x is preferably equal to 4.

According to one particular embodiment of the invention, in formula (2), the $R_2$ group represents an alkyl radical comprising from 12 to 18 carbon atoms.

According to one even more preferred embodiment of the invention, in formula (2), Y denotes an oxygen atom, the $R_1$ group represents a methyl, the $R_2$ group represents an alkyl radical comprising from 12 to 18 carbon atoms, and x represents an integer between 3 and 25, and x is preferably equal to 4.

According to one particular embodiment of the invention, the hydrophobic monomer of formula (2) is tetraethoxylated (4EO) lauryl methacrylate, corresponding to the compound of formula (2) in which the Y group denotes O, the $R_2$ group represents and alkyl radical comprising 12 carbon atoms and x is equal to 4.

Preferably, the monomer with a hydrophobic group is tetraethoxylated lauryl methacrylate.

According to one particular embodiment of the invention, the copolymer (c) may comprise at least one monomer of formula (2) in which x is equal to 0, with Y representing an oxygen atom, the $R_1$ group representing a methyl, and the $R_2$ group representing an alkyl radical comprising from 12 to 18 carbon atoms.

In this embodiment, the monomer with a hydrophobic group is preferably lauryl methacrylate.

According to one particular embodiment, the copolymer (c) comprises at least one monomer of formula (2) in which x is equal to 0, with Y preferably denoting an oxygen atom, the $R_1$ group representing a methyl, and the $R_2$ group representing an alkyl radical comprising from 12 to 18 carbon atoms, and at least one monomer of formula (2) in which Y denotes an oxygen atom, the $R_1$ group represents a methyl, the $R_2$ group represents an alkyl radical comprising from 12 to 18 carbon atoms, and x represents an integer between 3 and 25, and x is preferably equal to 4.

Preferably, the copolymer (c) comprises, as monomers with a hydrophobic group, lauryl methacrylate and tetraethoxylated lauryl methacrylate.

The copolymer(s) (c) also comprise at least one ethylenically unsaturated monomer, which does not comprise any hydrophobic groups, preferably corresponding to the following general formula (3):

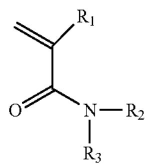
(3)

in which $R_1$ denotes a hydrogen atom or a linear or branched $C_1$-$C_4$ alkyl radical, $R_1$ preferably denotes a hydrogen atom, $R_2$ denotes a linear or branched $C_1$-$C_4$ alkyl radical and $R_3$ denotes a linear or branched $C_1$-$C_4$ alkyl radical and $R_2$ and $R_3$ preferably denote a methyl.

The ethylenically unsaturated monomer which does not comprise any hydrophobic groups is chosen from (meth)acrylamides such as acrylamide, (meth)acrylic acids and the esters ((meth)acrylates) thereof, such as 2-hydroxyethyl acrylate, vinylpyrrolidones, N—($C_1$-$C_4$)alkylacrylamides, and N,N-di($C_1$-$C_4$)alkylacrylamides such as N,N-dimethylacrylamide.

Preferably, the ethylenically unsaturated monomer which does not comprise any hydrophobic groups is N,N-dimethylacrylamide.

Preferably, the copolymer (c) is chosen from the copolymers of 2-acrylamido-2-methylpropanesulfonic acid, preferably completely salified, of N,N-dimethylacrylamide, of tetraethoxylated lauryl methacrylate and of lauryl methacrylate, preferably crosslinked, such as for example the copolymer sold under the name Sepimax Zen® by SEPPIC, with INCI name Polyacrylate crosspolymer-6.

Advantageously, the total amount of copolymer(s) (c) comprising at least one monomer of 2-acrylamido-2-methylpropanesulfonic acid, at least one monomer with a hydrophobic group and at least one ethylenically unsaturated monomer which does not comprise any hydrophobic groups in the composition ranges from 0.001 to 20% by weight, preferably from 0.001 to 15% by weight, more preferably from 0.01 to 10% by weight, even more preferably from 0.05 to 5% by weight, better from 0.1 to 2% by weight, even better from 0.1 to 1% by weight, still even better from 0.2 to 0.6% by weight relative to the total weight of the composition.

Advantageously, the total amount of polyacrylate crosspolymer-6 in the composition ranges from 0.001 to 20% by weight, preferably from 0.001 to 15% by weight, more preferably from 0.01 to 10% by weight, even more preferably from 0.05 to 5% by weight, better from 0.1 to 2% by weight, even better from 0.1 to 1% by weight, still even better from 0.2 to 0.6% by weight relative to the total weight of the composition.

Polyol (d)

According to the present invention, the composition comprises at least one polyol (d).

Herein, the term "polyol" relates to an alcohol having two or more hydroxy groups and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The polyol (d) may be a $C_{2-12}$ polyol, preferably a $C_{2-9}$ polyol, more preferably a $C_{2-6}$ polyol, comprising at least 2 hydroxy groups, and preferably from 2 to 5 hydroxy groups.

The polyol (d) may be a natural or synthetic polyol. The polyol may have a linear, branched or cyclic molecular structure.

The polyol (d) may be selected from glycerins and derivatives thereof, and glycols and derivatives thereof, and mixtures thereof. The polyol (d) may be selected from the group consisting of glycerin, diglycerin, polyglycerin, ethylene glycol, diethylene glycol, polyethylene glycol, propylene glycol, dipropylene glycol, polypropylene glycol, butylene glycol, pentylene glycol, hexylene glycol, 1,2-propanediol, 1,3-propanediol, and 1,5-pentanediol and mixtures thereof.

It may be preferable that the polyol (d) have 3 or more carbon atoms, and be selected from the group consisting of glycerin, ethylene glycol, polyethylene glycol, propylene glycol, dipropylene glycol, butylene glycol, pentylene glycol, hexylene glycol and mixtures thereof.

Preferably, the polyol(s) (d) is selected from $C_{2-12}$ polyols, preferably $C_{2-9}$ polyols, more preferably $C_{2-6}$ polyol, comprising at least 2 hydroxy groups, and preferably from 2 to 5 hydroxy groups and mixtures thereof, more preferably from the group consisting of glycerin and derivatives thereof, and glycols and derivatives thereof, and mixtures thereof, even more preferably from the group consisting of glycerin, diglycerin, polyglycerin, ethylene glycol, diethylene glycol, polyethylene glycol, propylene glycol, dipropylene glycol, polypropylene glycol, butylene glycol, pentylene glycol, hexylene glycol, 1,2-propanediol, 1,3-propanediol, and 1,5-pentanediol and mixtures thereof, better from the group consisting of glycerin, propylene glycol and mixtures thereof.

Advantageously, the total amount of polyol(s) (d) in the composition ranges from 5 to 60% by weight, preferably from 10 to 55% by weight, more preferably from 15 to 50% by weight, even more preferably from 20 to 45% by weight, better from 25 to 45% by weight, even better from 30 to 45% by weight relative to the total weight of the composition.

Advantageously, the total amount of polyol(s) (d) selected from $C_{2-6}$ polyols in the composition ranges from 5 to 60% by weight, preferably from 10 to 55% by weight, more preferably from 15 to 50% by weight, even more preferably from 20 to 45% by weight, better from 25 to 45% by weight, even better from 30 to 45% by weight relative to the total weight of the composition.

Silicone (e)

The composition according to the present invention may also include at least one silicone (e) different from silicones (a) and aminosilicones (b) as defined previously.

The silicones (e) may be solid or liquid at 25° C. and atmospheric pressure ($1.013\times10^5$ Pa), and volatile or non-volatile.

The silicones (e) that may be used may be soluble or insoluble in the composition according to the invention; they may be in the form of oil, wax, resin or gum.

Silicones are notably described in detail in Walter Noll's *Chemistry and Technology of Silicones* (1968), Academic Press.

The composition may contain one or more silicones that are liquid at 25° C. and atmospheric pressure ($1.013\times10^5$ Pa).

The volatile silicones may be chosen from those with a boiling point of between 60° C. and 260° C. (at atmospheric pressure) and more particularly from linear polydialkylsiloxanes containing 2 to 9 silicon atoms, which generally have a viscosity of less than or equal to $5\times10^{-6}$ $m^2/s$ at 25° C., such as decamethyltetrasiloxane.

Other silicones belonging to this category are described in the article published in Cosmetics and Toiletries, Vol. 91, January 76, pages 27-32—Todd & Byers *Volatile silicone fluids for cosmetics*; mention may be made of the product sold under the name SH 200 by the company Toray Silicone.

Among the non-volatile silicones, mention may be made, alone or as a mixture, of polydialkylsiloxanes and notably polydimethylsiloxanes (PDMS), silicone gums and resins, and also organopolysiloxanes (or organomodified polysiloxanes, or alternatively organomodified silicones) which are polysiloxanes including in their structure one or more organofunctional groups, generally attached via a hydrocarbon-based group, and preferably chosen from alkoxy groups and polyoxyethylene or polyoxypropylene groups.

Among the organomodified silicones, mention may be made of organopolysiloxanes including:

- polyoxyethylene and/or polyoxypropylene groups optionally including $C_6$-$C_{24}$ alkyl groups, such as dimethicone copolyols, and notably those sold by the company Dow Corning under the name DC 1248 or the oils Silwet® L 722, L 7500, L 77 and L 711 from the company Union Carbide; or alternatively (C12)alkylmethicone copolyols, and notably those sold by the company Dow Corning under the name Q2-5200;
- thiol groups, such as the products sold under the names GP 72 A and GP 71 from Genesee;
- alkoxylated groups, such as the product sold under the name Silicone Copolymer F-755 by SWS Silicones and Abil Wax® 2428, 2434 and 2440 by the company Goldschmidt;
- hydroxylated groups, for instance polyorganosiloxanes bearing a hydroxyalkyl function;
- acyloxyalkyl groups, such as the polyorganosiloxanes described in patent U.S. Pat. No. 4,957,732;
- anionic groups of the carboxylic acid type, as described, for example, in EP 186 507, or of the alkylcarboxylic type, such as the product X-22-3701E from the company Shin-Etsu; or alternatively of the 2-hydroxyalkylsulfonate or 2-hydroxyalkylthiosulfate type, such as the products sold by the company Goldschmidt under the names Abil® S201 and Abil® S255.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200, with a viscosity of 60 000 $mm^2/s$;
- the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Products that may be used more particularly in accordance with the invention are mixtures such as:

- mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning,
- mixtures formed from a polydimethylsiloxane with a hydroxy-terminated chain, or dimethiconol (CTFA), and from a polydimethylsiloxane, also known as dimethicone (CTFA), such as the product Xiameter® PMX-1503 Fluid sold by the company Dow Corning.

Preferably, the composition further comprises at least one silicone (e) different from silicones (a) and aminosilicones (b), and more preferably at least two different silicones (e).

Preferably, the silicone(s) (e) selected from:

- polydialkylsiloxanes, more preferably from polydimethylsiloxanes, even more preferably from polydimethylsiloxanes bearing trimethylsilyl end groups,
- polydimethylsiloxanes with a hydroxy-terminated chain (dimethiconol), and
- mixtures thereof.

More preferably, the composition comprises one or more polydimethylsiloxanes and one or more dimethiconols.

Advantageously, the total amount of silicone(s) (e) in the composition ranges from 0.1 to 45% by weight, preferably from 1 to 40% by weight, more preferably from 5 to 35% by weight, even more preferably from 10 to 35% by weight, better from 15 to 30% by weight, even better from 20 to 25% by weight, relative to the total weight of the composition.

Advantageously, the total amount of silicone(s) (e) selected from polydimethylsiloxanes, dimethiconols, and their mixtures in the composition ranges from 0.1 to 45% by weight, preferably from 1 to 40% by weight, more preferably from 5 to 35% by weight, even more preferably from 10 to 35% by weight, better from 15 to 30% by weight, even better from 20 to 25% by weight, relative to the total weight of the composition.

Preferably, the silicone (e) is not chosen from cyclic polydialkylsiloxanes including from 3 to 7 and in particular 4 to 5 silicon atoms, such as octamethylcyclotetrasiloxane and decamethylcyclopentasiloxane.

Preferably the composition does not comprise decamethylcyclopentasiloxane, meaning the composition comprises less than 0.1% of decamethylcyclopentasiloxane, better, the composition comprises 0% of decamethylcyclopentasiloxane.

Alkane

The composition according to the present invention may also include at least one alkane, preferably at least one volatile alkane.

More particularly, the volatile alkanes may have a flash point ranging from 40° C. to 102° C., preferably ranging from 40° C. to 55° C. and preferentially ranging from 40° C. to 50° C.

The alkanes may in particular be chosen from alkanes containing from 8 to 16 carbon atoms, and mixtures thereof, and in particular:

branched $C_8$-$C_{16}$ alkanes such as $C_8$-$C_{16}$ isoalkanes (also known as isoparaffins), isododecane, isodecane and isohexadecane, and, for example, the oils sold under the trade name Isopar or Permethyl, linear alkanes, for instance n-dodecane (C12) and n-tetradecane (C14) sold by Sasol under the respective references Parafol 12-97 and Parafol 14-97, and also mixtures thereof, the undecane-tridecane mixture (Cetiol UT), the mixtures of n-undecane (C11) and of n-tridecane (C13) obtained in Examples 1 and 2 of patent application WO 2008/155059 from the company Cognis, and mixtures thereof.

Preferably, the composition according to the invention further comprises at least one alkane, preferably selected from alkanes comprising from 8 to 16 carbon atoms and mixtures thereof, more preferably selected from branched $C_8$-$C_{16}$ alkanes, even more preferably from $C_8$-$C_{16}$ isoalkanes such as isododecane, isodecane, isohexadecane, and mixtures thereof, more preferably from isododecane.

Advantageously, the total amount of alkane(s) in the composition ranges from 0.1 to 25% by weight, from 0.1 to 20% by weight, preferably from 0.5 to 15% by weight, more preferably from 1 to 10% by weight relative to the total weight of the composition.

The composition according to the invention is preferably aqueous.

The water content may range from 1% to 70% by weight, preferably from 10% to 60% by weight, more preferably from 15% to 50% by weight, even more preferably from 20 to 45% by weight, relative to the total weight of the composition according to the invention.

Preferably, the composition according to the invention comprises:

(a) at least one silicone of formula (X) chosen from the group consisting of phenyl trimethicone, diphenyl dimethicone, or phenyl methicone, and mixtures thereof, (b) at least one aminosilicone selected from the group consisting of amodimethicones, (c) at least one polyacrylate crosspolymer-6, (d) at least one polyol is selected from the group consisting of $C_{2-12}$ polyols, comprising at least 2 hydroxy groups, and preferably from the group consisting of glycerin, diglycerin, polyglycerin, ethylene glycol, diethylene glycol, polyethylene glycol, propylene glycol, dipropylene glycol, polypropylene glycol, butylene glycol, pentylene glycol, hexylene glycol, 1,2-propanediol, 1,3-propanediol, and 1,5-pentanediol and mixtures thereof.

Other Ingredients

The composition according to the present invention may also include at least one optional or additional ingredient.

The optional or additional ingredient(s) may be selected from the group consisting of anionic, non-ionic or amphoteric polymers; anionic, non-ionic or amphoteric surfactants; organic or inorganic UV filters; peptides and derivatives thereof; protein hydrolyzates; swelling agents and penetrating agents; agents for combating hair loss; anti-dandruff agents; natural or synthetic thickeners for water or oils; suspending agents; sequestering agents; dyes; pearlescent agents, pigments, opacifying agents, sunscreen agents; vitamins or provitamins; fragrances; preservatives, co-preservatives, stabilizers; and mixtures thereof.

The amount of the optional or additional ingredient(s) is not limited, but may be from 0.01 to 30% by weight, preferably from 0.1 to 20% by weight, and more preferably from 1 to 10% by weight, relative to the total weight of the composition according to the present invention.

The composition according to the present invention may be leave-in type or rinse-off type, preferably leave-in type.

Use

The composition according to the present invention may preferably be used as a cosmetic composition. The cosmetic composition may be used for treating keratin fibres. The keratin fibres may be hair, eyebrows, eyelashes and the like.

In particular, the composition according to the present invention may be intended for application onto keratin fibres such as hair. Thus, the composition according to the present invention can be used for a cosmetic process for keratin fibres.

The composition according to the present invention may preferably be used as a cosmetic composition. The cosmetic composition may be used for treating keratin fibres. The keratin fibres may be hair, eyebrows, eyelashes and the like.

Thus, the present invention also relates to the use of a cosmetic composition as previously defined for the treatment of keratin fibres, preferably human keratin fibres, such as hair, eyebrows, eyelashes and the like, even more preferably hair.

Process

In particular, the composition according to the present invention may be intended for application onto keratin fibres such as hair. Thus, the composition according to the present invention can be used for a cosmetic process for keratin fibres.

The present invention also relates to a cosmetic process for treating keratin fibres, preferably hair, comprising the step of applying the cosmetic composition according to the present invention to the keratin fibres.

The keratin fibres to which the composition according to the present invention has been applied can be left for an appropriate time which is required to treat the keratin fibres.

The composition according to the present invention may be rinsed or not. When the composition is rinsed, the time length for the treatment is not limited, but it may range from 1 minute to 10 minutes, preferably from 1 minute to 5 minutes.

Preferably, the composition of the invention is not rinsed.

The keratin fibres may be treated at room temperature. Alternatively, the keratin fibres can be heated at 15° C. to 45° C., preferably 20° C. to 40° C., more preferably 25° C. to 35° C., and even more preferably 27° C. to 35° C., before and/or during and/or after the step of applying the composition according to the present invention onto the keratin fibres.

The keratin fibres to which the composition according to the present invention has been applied may or may not be rinsed, preferably they are not rinsed following application of the composition.

The process, preferably cosmetic process, according to the present invention can provide keratin fibres such as hair with improved conditioning and manageability cosmetic effects such as smoothness (e.g., smooth combing even if the keratin fibres are wet, and smooth feeling to touch when the keratin fibres are dry), softness, shine, ease of styling, ease of detangling and volume down control (therefore, it can be easy to style the shape of keratin fibres, due to anti-frizz properties of the composition according to the present invention). The term "volume down" means that spreading of keratin fibres is reduced or controlled, and therefore, the style of the keratin fibres can be well-controlled.

In particular, the process according to the present invention can provide keratin fibres such as hair with higher level of smoothness, softness, shine, volume control and the like.

Device

A subject of the present invention relates to a dropper device suitable for applying the cosmetic composition according to invention to the keratin fibres such as the hair and delivering said composition in a dropwise manner.

In the present description, the expressions “dropper” and “pipette” are equivalent.

In an embodiment, the cosmetic composition according to the invention may be packaged in a dropper device suitable for applying said cosmetic composition to the keratin fibres, preferably hair, wherein said device comprises ajar, bottle or container containing said cosmetic composition, and a dropper or pipette, and wherein it delivers said cosmetic composition in a dropwise manner.

The dropwise delivery of the composition permits a controlled distribution of the composition via a regular sequence of drops as opposed to an uncontrolled delivery by jet. Thus, dropwise delivery of the composition enables quantity control in product dispensing.

In an embodiment, the dropper or pipette is adapted to be mounted onto the jar, bottle or container via removable joining means and/or releasable fastening means.

In some embodiments, the composition is delivered in suitable quantity to the user using a dropper device comprising a jar, bottle or container and a dropper or pipette.

Herein, “suitable quantity” means enough of the composition is delivered for use, without overdistribution of the composition.

The jar, bottle or container may be made from glass or plastic, or from any other material appropriate as a container for cosmetic compositions.

In an embodiment, the composition may be stored within the body of the jar, bottle or container and dispensed through the tip of the dropper or pipette.

In another embodiment, the composition of the invention is stored in a dropper device comprising a container containing said composition, a closure member entirely screwed onto the container, a pipette attached to the closure member, and a compressible chamber linked to the pipette and configured to expel the product from the pipette when compressed and to suck the product into the pipette when relaxed. Such kind of dropper device is also disclosed in WO0147784.

In a preferred embodiment, the dropper device is suitable for delivering a composition according to the invention that is fluid to semi-fluid, more preferably a composition according to the invention that is fluid.

Advantageously, the different portions making up the dropper device are connected in such a way as to prevent leakage of the composition according to the invention during use.

The composition according to the invention is not limited to be used with the dropper device disclosed above. Other actuating mechanism of dropper device could be used, or the composition can be packaged in a standard jar, bottle or container.

The present invention also relates to a process for applying the composition according to the invention using a dropper device as defined previously onto the hair, comprising the following steps:

(i) shaking the jar, bottle or container containing at least the composition according to the invention, (ii) applying a pressure on the compressible chamber linked to the dropper or pipette for sucking up the composition according to the invention into the dropper or pipette, (iii) removing the dropper or pipette from the jar, bottle or container and applying another pressure on the compressible chamber linked to the dropper or pipette to expel the composition according to the invention in a controlled manner, for example onto the hair or the palm of the hand, then (iv) spreading with fingers the composition onto the hair and smoothing it until homogenisation.

EXAMPLES

The present invention will be described in a more detailed manner by way of examples. However, these examples should not be construed as limiting the scope of the present invention.

Example 1

Composition A according to invention and comparative composition B were prepared from the ingredients indicated in the table 1 below, the amounts of which are expressed in grams of AM per 100 g, unless otherwise mentioned (AM meaning “active material”):

TABLE 1

| Ingredients | Composition A (invention) | Composition B (comparative) |
|---|---|---|
| Amodimethicone | 2.4 | 2.4 |
| Dimethicone | 19.4 | 19.4 |
| Dimethiconol | 2.6 | 2.6 |
| Glycerin | 4.1 | 4.1 |
| Isododecane | 3.5 | 3.5 |
| Mica/Titane | 0.02 | 0.02 |
| Phenyl Trimethicone | 5.0 | 5.0 |
| Polyacrylate Crosspolymer-6 (1) | 0.4 | — |
| Acrylates/C10-30 alkylacrylate Crosspolymer (2) | — | 0.4 |
| Propylene Glycol | 33.0 | 33.0 |
| Trideceth-10 | 0.2 | 0.2 |
| Trideceth-5 | 0.9 | 0.9 |
| Preservatives | qs | qs |
| Water | Qsp 100 | Qsp 100 |

(1) sold by company SEPPIC under the brand name Seppimax Zen ®

(2) sold by company Lubrizol under the brand name Pemulen TR1 Polymer

Protocol of Application

Swatches (27 cm) of Caucasian double-bleached hair were washed with a shampoo, rinsed and dried.

The compositions A and B thus obtained were then applied on the swatches according to a ratio of 3 g of composition per gram of hair. After 2 minutes, the swatches were dried.

Instrumental Evaluation

Characterisation of the surface state of dry hair was conducted through a sliding test using a sliding bench in a controlled environment (23° C., 50% HR). The test was repeated on three hair swatches for each composition.

A mobile swatch, attached to a sliding bench, was caused to move in a horizontal rectilinear manner between two other fixed swatches. The force needed to make the swatch to slide between the two others was measured with the aid of an electronic gauge linked to a driving arm. The measurement was made from roots to tips.

The average force (over 3 measurements) was calculated, and the evolution of the sliding force was recorded to quantify the surface state (homogeneous or not), along the fibre. The lower the sliding force, the more homogeneous the surface state of the hair. The more homogeneous the surface state, the smoother the hair to the touch.

The results are collated in the table 2 below:

TABLE 2

| Compositions | Average Fmax (N) | Standard deviation (N) |
|---|---|---|
| A (invention) | 0.77 | ±0.01 |
| B (comparative) | 1.02 | ±0.02 |

The sliding force for composition A according to the invention is significantly lower than the sliding force for comparative composition B. Thus, the surface state is more homogeneous and the hair is smoother to the touch when treated with composition A according to the invention.

Composition A possesses good usage properties: indeed, it is a translucent composition, which has a singular, pleasant texture when applied.

The hair treated with composition A is smooth, shiny, straight, detangled and easy to style.

Moreover, composition A possesses adequate viscosity to be delivered with a dropper device in a controlled and cost-saving manner.

Example 2

Composition C according to the invention was prepared from the ingredients indicated in the table 3 below, the amounts of which are expressed in grams of AM per 100 g, unless otherwise mentioned (AM meaning “active material”):

TABLE 3

| Ingredients | Composition C (invention) |
|---|---|
| Amodimethicone | 2.4 |
| Dimethicone | 19.4 |
| Dimethiconol | 2.6 |
| Glycerin | 4.1 |
| Isododecane | 3.5 |
| Phenyl Trimethicone | 5.0 |
| Polyacrylate Crosspolymer-6 (1) | 0.4 |
| Propylene Glycol | 33.0 |
| Trideceth-10 | 0.2 |
| Trideceth-5 | 0.9 |
| Preservatives | qs |
| Water | Qsp 100 |

Protocol of Application

Swatches (27 cm) of Caucasian double-bleached hair were washed with a shampoo, rinsed and dried.

The composition C thus obtained was applied on the swatches according to a ratio of 3 g of composition per gram of hair. After 2 minutes, the swatches were dried.

The dropper device was used to deliver composition C.

Results

Composition C possesses good usage properties: indeed, it is a translucent to transparent composition, which has a singular, pleasant texture when applied.

The hair treated with composition C is smooth, shiny, straight, detangled and easy to style.

Moreover, composition C possesses adequate viscosity to be delivered with a dropper device in a controlled and cost-saving manner.

The invention claimed is:

1. A cosmetic composition comprising:

(a) at least one silicone of formula (X) below:

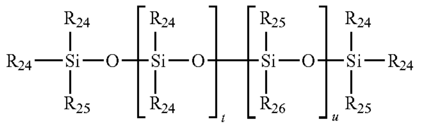

(X)

in which:

$R_{24}$, which is identical or different, denotes a $C_1$-$C_{10}$ alkyl radical;

$R_{26}$, which is identical or different, denotes an aryl group, it being possible for this aryl group to comprise one or more optionally substituted aryl rings;

$R_{25}$, which is identical or different, denotes $R_{26}$, $R_{24}$ or —$OSi(R_{24})$ 3;

t varies from 0 to 1000;

u varies from 1 to 1000;

and the sum of t+u can vary from 1 to 2000;

(b) at least one aminosilicone;

(c) at least one copolymer comprising at least one monomer of 2-acrylamido-2-methylpropanesulfonic acid, at least one monomer with a hydrophobic group that is a hydrocarbon-based, branched or unbranched, saturated or unsaturated fatty chain comprising from 6 to 50 carbon atoms, and at least one ethylenically unsaturated monomer which does not comprise any hydrophobic groups that is a hydrocarbon-based, branched or unbranched, saturated or unsaturated fatty chain comprising from 6 to 50 carbon atoms; and (d) at least one polyol.

2. The composition according to claim 1, wherein the total amount of the at least one silicon (a) in the composition ranges from 1 to 40% by weight relative to the total weight of the composition.

3. The composition according to claim 2, wherein the at least one aminosilicone (b) is selected from amodimethicones.

4. The composition according to claim 2, wherein the total amount of the at least one aminosilicone (b) in the composition ranges from 0.01 to 30% by weight relative to the total weight of the composition.

5. The composition according to claim 1, wherein the at least one aminosilicone (b) is selected from amodimethicones.

6. The composition according to claim 5, wherein the total amount of the at least one aminosilicone (b) in the composition ranges from 0.01 to 30% by weight relative to the total weight of the composition.

7. The composition according to claim 1, wherein the total amount of the at least one aminosilicone (b) in the composition ranges from 0.01 to 30% by weight relative to the total weight of the composition.

8. The composition according to claim 1, wherein the at least one copolymer (c) comprises at least one monomer corresponding to the general formula (1) below:

(1)

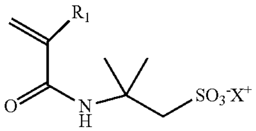

in which $X^+$ denotes a cationic counterion or a mixture of cations; $R_1$ denotes a hydrogen atom or a linear or branched $C_1$-$C_6$ alkyl radical.

9. The composition according to claim 1, wherein the at least one copolymer (c) comprises at least one monomer with a hydrophobic group chosen from the acrylates or acrylamides of formula (2) below:

(2)

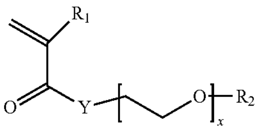

in which $R_1$ denotes a hydrogen atom or a linear or branched $C_1$-$C_6$ alkyl radical; Y denotes O or NH; $R_2$ denotes a hydrocarbon-based radical comprising from 6 to 50 carbon atoms; x denotes a number ranging from 0 to 100.

10. The composition according to claim 1, wherein the at least one copolymer (c) comprises at least one monomer corresponding to the general formula (3) below:

(3)

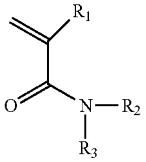

in which $R_1$ denotes a hydrogen atom or a linear or branched $C_1$-$C_4$ alkyl radical, $R_1$ preferably denotes a hydrogen atom, $R_2$ denotes a linear or branched $C_1$-$C_4$ alkyl radical and $R_3$ denotes a linear or branched $C_1$-$C_4$ alkyl radical.

11. The composition according to claim 1, wherein the total amount of the at least one copolymer (c) in the composition ranges from 0.001 to 20% by weight relative to the total weight of the composition.

12. The composition according to claim 1, wherein the at least one polyol (d) is selected from $C_2$-12 polyols comprising at least 2 hydroxy groups and mixtures thereof.

13. The composition according to claim 1, wherein the total amount of the at least one polyol (d) in the composition ranges from 5 to 60% by weight relative to the total weight of the composition.

14. The composition according to claim 1, wherein the composition further comprises at least one silicone (e) different from the at least one silicon (a) and the at least one aminosilicone (b).

15. The composition according to claim 14, wherein the total amount of the at least one silicon (e) in the composition ranges from 0.1 to 45% by weight, relative to the total weight of the composition.

16. The composition according to claim 1, wherein the composition further comprises at least one alkane.

17. The composition according to the preceding claim 16, wherein the total amount of the at least one alkane in the composition ranges from 0.1 to 25% by weight relative to the total weight of the composition.

18. A cosmetic process for treating keratin fibres comprising the step of applying the cosmetic composition according to claim 1 to the keratin fibres.

19. The cosmetic process according to claim 18, wherein the keratin fibres are hair.

20. A dropper device suitable for applying the cosmetic composition according to claim 1 to the keratin fibres wherein said device comprises a jar, bottle or container containing said cosmetic composition, and a dropper or pipette, and wherein it delivers said cosmetic composition in a dropwise manner.

* * * * *